United States Patent [19]

Vogel

[11] 4,045,455
[45] Aug. 30, 1977

[54] PROCESS FOR SEPARATING 1,5-DINITROANTHRAQUINONE AND 1,8-DINITROANTHRAQUINONE FROM DINITROANTHRAQUINONE MIXTURES

[75] Inventor: Axel Vogel, Cologne, Germany

[73] Assignee: Bayer Aktiengesellschaft, Leverkusen, Germany

[21] Appl. No.: 533,595

[22] Filed: Dec. 17, 1974

[30] Foreign Application Priority Data

Jan. 3, 1974 Germany .............. 2400164

[51] Int. Cl.$^2$ .............................................. C09B 1/00
[52] U.S. Cl. .................................................. 260/369
[58] Field of Search ................ 260/369, 378, 688, 707

[56] References Cited

U.S. PATENT DOCUMENTS

| 2,435,314 | 2/1948 | Kokatnur | 260/688 X |
| 3,163,657 | 12/1964 | Morgan et al. | 260/369 X |
| 3,506,725 | 4/1970 | Sturm et al. | 260/707 X |
| 3,818,052 | 6/1974 | Hohmann et al. | 260/378 |
| 3,923,845 | 12/1975 | Bantel et al. | 260/369 |

FOREIGN PATENT DOCUMENTS 72,685  12/1893  Germany

*Primary Examiner* — Allen B. Curtis
*Attorney, Agent, or Firm* — Burgess, Dinklage & Sprung

[57] ABSTRACT

The present invention relates to a process for separating substantially pure 1,5-dinitroanthraquinone and substantially pure 1,8-dinitroanthraquinone from anthraquinone dinitration mixtures containing 1,5- and 1,8-dinitroanthraquinone, whereby such mixtures are treated with a mixture of concentrated nitric acid and an inert organic solvent, the insoluble 1,5-dinitroanthraquinone is separated off and the 1,8-dinitroanthraquinone isolated from the remaining mother liquor.

14 Claims, No Drawings

PROCESS FOR SEPARATING 1,5-DINITROANTHRAQUINONE AND 1,8-DINITROANTHRAQUINONE FROM DINITROANTHRAQUINONE MIXTURES

This invention relates to a process for separating 1,5-dinitroanthraquinone and 1,8-dinitroanthraquinone from anthraquinone dinitration mixtures.

It is known that dinitroanthraquinones can be obtained by nitrating anthraquinones with nitric acid in sulphuric acid or with excess nitric acid (Methoden der organischen Chemie [Houben-Weyl], 4th Edition (1971), Stuttgart, Vol. X/1, page 615; DOS 2,248,704).

This process generally gives mixtures of the dinitroanthraquinones, more especially mixtures containing 1,5-; 1,8-; 1,6- and 1,7-dinitroanthraquinone. These mixtures are difficult to separate into the pure individual compounds.

It has now surprisingly been found that substantially pure 1,5-dinitroanthraquinone and, optionally in a second fraction, substantially pure 1,8-dinitroanthraquinone can be separated from mixtures of the kind in question by treating these mixtures with a mixture of concentrated nitric acid and an inert organic solvent at temperatures in the range from 0° to 90° C and preferably at temperatures in the range from 40° to 80° C.

The dinitration mixture is preferably treated with a mixture of (based on 1 part by weight of nitration mixture) 0.4 to 20 parts by weight and preferably 0.6 to 10 parts by weight of inert organic solvents and 1.5 to 5 parts by weight, preferably 2.5 to 4 parts by weight, of concentrated nitric acid, more especially 92 to 100% and preferably 95 to 100% nitric acid.

Under these conditions, the 1,5-dinitroanthraquinone remains substantially undissolved in the mixture of inert organic solvent and nitric acid, whilst at the same time the 1,8-dinitroanthraquinone and the other secondary products of the nitration reaction are dissolved. The substantially pure 1,5-dinitroanthraquinone can readily be isolated by filtration, decantation, centrifuging or similar separation techniques, washed with one of the aforementioned inert organic solvents, optionally in admixture with highly concentrated nitric acid and/or water, and subsequently dried. In general, the highly concentrated nitric acid used has a concentration in the range from 92 to 100% by weight and preferably in the range from about 95 to 100% by weight, and is employed in a quantity of up to 75% by volume and preferably in a quantity of up to 50% by volume of the final washing solution.

The 1,8-dinitroanthraquinone can be isolated from the mother liquor by different methods, for example the solution may be cooled to temperatures of from −20° to +40° C and preferably to temperatures of from −10° to +20° C, and the 1,8-dinitroanthraquinone precipitated filtered off. However, the solubility of the 1,8-dinitroanthraquinone in the solution mixture may be reduced by diluting the nitric acid, for example by adding water, the ratio by weight of nitric acid to water generally being adjusted to between 92 : 8 and 75 : 25 and preferably to between 90 : 10 and 85 : 15. In addition, the nitric acid may be washed out of the solution mixture, for example by adding water, for which purpose at least 35 parts by weight of water and preferably at least 50 parts by weight of water are used per 100 parts by weight of nitric acid, and hence the 1,8-dinitroanthraquinone precipitated, optionally together with the 1,6-/1,7-dinitroanthraquinone fraction. Finally, the mother liquor may also be concentrated by distillation and either the inert organic solvent and/or the nitric acid initially distilled off either wholly or in part and the 1,8-dinitroanthraquinone subsequently isolated or precipitated and isolated by the methods described above.

In the context of the invention, inert organic solvents are solvents of the type which undergo little or no reaction with the nitrating agent under the reaction conditions.

Examples of solvents suitable for use in the process according to the invention are aliphatic and alicyclic hydrocarbons having up to 12 carbon atoms and preferably having up to 6 carbon atoms which may be substituted either once or several times by halogen (fluorine, chlorine, bromine, iodine) or by the nitro group. Examples of solvents such as these include methane, ethane, propane, butane, pentane, hexane, cyclopentane and cyclohexane. In addition to the straightchain isomers, this exemplary list naturally includes the branched isomers as well, and also alkyl-substituted cycloaliphatic hydrocarbons.

It is preferred to use chlorine-substituted hydrocarbons, for example methylene chloride, chloroform, carbon tetrachloride, 1,1-dichloroethane, 1,2-dichloroethane, 1,1,2-trichloroethane, 1,1,2,2-tetrachloroethane, pentachloroethane, 1,2-dichloropropane and 1,3-dichloropropane, 1,2,3-trichloropropane, 1,1,2,3-and 1,1,3,3-tetrachloropropane, 1,1,1,3,3,-pentachloropropane, 1,1,1,2,3,3- and 1,1,1,2,2,3-hexachloropropane, 1,1,1,2,2,3,3-and 1,1,1,2,3,3,3-heptachloropropane, 1,2- and 1,4-dichlorobutane.

Examples of bromine-substituted hydrocarbons include methylene bromide, bromoform, tetrabromomethane, 1,2-dibromomethane and 1,2-dibromopropane.

It is also possible to use, in the process according to the invention, hydrocarbons which are substituted for example by fluorine or by more than one halogen, for example fluorotrichloromethane, difluorodichloromethane, difluorodibromomethane, 1,1,2-trifluoro-1,2,2-trichloroethane and perfluoro-1,3-dimethyl cyclohexane.

Among the hydrocarbons substituted by the nitro group, reference is made in particular to nitromethane and nitroethane.

In addition to nitric acid, the solution mixture may also contain other mineral acids, preferably the mineral acids used for dinitration of anthraquinones, such as for example sulphuric acid, phosphoric acid or hydrofluoric acid.

Dinitroanthraquinones of the type mentioned above are important intermediate products for the production of chlorine-substituted, amino-substituted, alkoxy-substituted, phenoxy-substituted and other substituted anthraquinones which are required for the production of anthraquinone dyes.

EXAMPLE 1 a. 20 g of a dinitroanthraquinone mixture of the following composition 40.5% of 1,5-dinitroanthraquinone (A), 7.7% of 1,6-dinitroanthraquinone (B), 8.4% of 1,7-dinitroanthraquinone (C) and 38.6% of 1,8-dinitroanthraquinone (D) are suspended in 50 ml of 1,2-dichloroethane. Following the addition of 50 ml of 98% HNO$_3$, the mixture is stirred for 1 hour at 60° C, filtered at 60° C and the filter residue washed with 20 ml of 1,2-dichloroethane and then with water and dried. 6.0 g of a product of the following composition are obtained:

94.3% of 1,5-dinitroanthraquinone, 0.3% of 1,6-dinitroanthraquinone, 0.4% of 1,7-dinitroanthraquinone 4.9% of 1,8-dinitroanthraquinone. 200 ml of water are stirred into the filtrate, the organic solvent distilled off and the deposit isolated by filtration, washed and dried. 14.0 g of a product of the following composition are obtained: 18.5% of (A), 10.6% of (B), 12.5% of (C) and 55.4% of (D).

b. 20 g of a dinitroanthraquinone mixture having the same composition as in (a) above are suspended at 20° C in 100 ml of methylene chloride. 50 ml of 98% HNO₃ are added and the mixture is stirred for 1 hour at 20° C. Undissolved fractions are filtered off at 20° C, and the filter residue is washed with 20 ml of methylene chloride and then with water and dried. 5.8 g of a product of the following composition are obtained: 94.7% of (A), 0.2% of (B), 0.2% of (C) and 4.7% of (D). 15 ml of water are stirred into the filtrate, the mixture stirred for 1 hour at 20° C and the deposit filtered off. After washing with 30 ml of methylene chloride, the product is washed with water until neutral. 9.5 g of a product of the following composition are obtained: 26.8% of (A), 0.5% of (B), 0.8% of (C), 71.2% of (D).

EXAMPLE 2 a. 200 g of a dinitroanthraquinone mixture consisting of 44% of (A), 6.3% of (B), 64% of (C) and 41% of (D), are stirred for 2 hours at 40° C with a mixture of 100 ml of methylene chloride, 410 ml of 95% nitric acid and 85 ml of 100% sulphuric acid. The undissolved fraction is filtered off at 40° C and the filter residue washed first with 4 × 50 ml of methylene chloride and then with water until neutral. 76.0 g of 1,5-dinitroanthraquinone with the following composition are obtained: 96% of (A), <0.5% of B, <0.5% of (C), 4.0% of (D). 45 ml of water are stirred at 20° C into the methylene chloride filtrate, the mixture stirred for 30 minutes and deposit subsequently filtered off at 20° C. After washing with 4 × 50 ml of methylene chloride, the product is washed with water until neutral and then dried. The yield comprises 34.1 g of 1,8-dinitroanthraquinone consisting of 6.1% of (A), <0.5% of (B), <0.5% of (C) and 93.3% of (D).

b. 200 g of a dinitroanthraquinone mixture having the same composition as in (2a) above are treated as in (2a) with methylene chloride, nitric acid and sulphuric acid and the 1,5-dinitroanthraquinone fraction filtered off. The methylene chloride filtrate is distilled through a 30 cm column first under normal pressure to remove the methylene chloride and then in vacuo to remove 67 ml of nitric acid. The distillation sump is cooled to 50° C and the deposit filtered off at that temperature. It is washed with water until neutral and then dried. The yield comprises 61.2 g of 1,8-dinitroanthraquinone consisting of 6.6% of (A), <0.5% of (B), <0.5% of (C) and 92.8% of (D).

(A = 1,5-dinitroanthraquinone;
B = 1,6-dinitroanthraquinone;
C = 1,7-dinitroanthraquinone;
D = 1,8-dinitroanthraquinone)

What we claim is:

1. A process for separating substantially pure 1,5-dinitroanthraquinone and substantially pure 1,8-dinitroanthraquinone from an anthraquinone dinitration mixture containing 1,5- and 1,8-dinitroanthraquinone which comprises adding to the dinitration mixtures a mixture of concentrated nitric acid and an inert organic solvent, said inert organic solvent being an aliphatic or cycloaliphatic hydrocarbon having up to 12 carbon atoms which can be substituted once or several times by halogen or by a nitro group, separating off the insoluble 1,5-dinitroanthraquinone from the resulting mixture and isolating the 1,8-dinitroanthraquinone from the resulting mother liquor.

2. A process as claimed in claim 1, in which the 1,5-dinitroanthraquinone is separated at a temperature of from 0° to 90° C.

3. A process as claimed in claim 2, in which the temperature is from 40° to 80° C.

4. A process as claimed in claim 1, in which the dinitration mixture is treated with from 1.5 to 5 parts by weight of from 92 to 100% HNO₃ and from 0.4 to 20 parts by weight inert solvent per part by weight of the dinitration mixture.

5. A process as claimed in claim 1, in which the inert solvent is an aliphatic chlorinated hydrocarbon.

6. A process as claimed in claim 5, in which the aliphatic chlorinated hydrocarbon is methylene chloride, 1,2-dichloroethane, 1,2-dichloropropane or 1,1,2,2-tetrachloroethane.

7. A process as claimed in claims 1, in which the 1,8-dinitroanthraquinone is isolated by precipitation from the mother liquor following the addition of water to the mother liquor.

8. A process as claimed in claim 1, in which the 1,8-dinitroanthraquinone is isolated by precipitation from the mother liquor following distilling off of some of the nitric acid in the mother liquor.

9. A process according to claim 1 wherein said inert organic solvent is selected from the group consisting of methylene chloride, chloroform, carbon tetrachloride, 1,1-dichloroethane, 1,2-dichloroethane, 1,1,2-trichloroethane, 1,1,2,2-tetrachloroethane, pentachloroethane, 1,2-dichloropropane.
1,3-dichloropropane, 1,2,3-trichloropropane, 1,1,2,3- and 1,1,3,3-tetrachloropropane, 1,1,1,3,3,-pentachloropropane, 1,1,1,2,3,3- and 1,1,1,2,2,3-hexachloropropane, 1,1,1,2,2,3,3-and 1,1,1,2,3,3,3-heptachloropropane, 1,2- and 1,4-dichlorobutane.

10. A process according to claim 1 wherein said inert organic solvent is selected from the group consisting of methylene bromide, bromoform, tetrabromomethane, 1,2-dibromomethane and 1,2-dibromopropane.

11. A process according to claim 1 wherein said inert organic solvent is a bromine-substituted hydrocarbon.

12. A process for separating substantially pure 1,5-dinitroanthraquinone and substantially pure 1,8-dinitroanthraquinone from an anthraquinone dinitration mixture containing 1,5- and 1,8-dinitroanthraquinone which consists essentially of adding to the dinitration mixtures with a mixture of concentrated nitric acid and an inert organic solvent, said inert organic solvent being an aliphatic or cycloaliphatic hydrocarbon having up to 12 carbon atoms which can be substituted once or several times by halogen or by a nitro group, separating off the insoluble 1,5-dinitroanthraquinone from the resulting mixture and isolating the 1,8-dinitroanthraquinone from the resulting mother liquor.

13. A process according to claim 12 wherein said organic solvent is selected from the group consisting of methylene chloride, chloroform, carbon tetrachloride, 1,1-dichloroethane, 1,2-dichloroethane, 1,1,2-trichloroethane, 1,1,2,2-tetrachloroethane, pentachloroethane, 1,2-dichloropropane, 1,3-dichloropropane, 1,2,3-trichloropropane, 1,1,2,3-and 1,1,3,3-tetrachloropropane, 1,1,1,3,3,-pentachloropropane, 1,1,1,2,3,3- and 1,1,1,2,2,3-hexachloropropane, 1,1,1,2,2,3,3-and 1,1,1,2,3,3,3-heptachloropropane, 1,2- and 1,4-dichlorobutane.

14. A process according to claim 12 wherein said organic solvent is selected from the group consisting of methylenebromide, bromoform, tetrabromomethane, 1,2-dibromomethane and 1,2-dibromopropane.

* * * * *